US011872221B2

(12) United States Patent
Chen et al.

(10) Patent No.: US 11,872,221 B2
(45) Date of Patent: Jan. 16, 2024

(54) TREATING UNTREATED OR TREATMENT-RESISTANT DIABETES WITH GLUCOKINASE ACTIVATOR

(71) Applicant: HUA Medicine (Shanghai) Ltd., Shanghai (CN)

(72) Inventors: Li Chen, Shanghai (CN); Shuang Ren, Shanghai (CN); Jiayi Zhang, Shanghai (CN)

(73) Assignee: HUA Medicine (Shanghai) Ltd., Shanghai (CN)

( * ) Notice: Subject to any disclaimer, the term of this patent is extended or adjusted under 35 U.S.C. 154(b) by 102 days.

(21) Appl. No.: 17/163,206

(22) Filed: Jan. 29, 2021

(65) Prior Publication Data

US 2021/0236486 A1 Aug. 5, 2021

Related U.S. Application Data

(60) Provisional application No. 62/968,441, filed on Jan. 31, 2020.

(51) Int. Cl.
| | | |
|---|---|---|
| *A61K 31/4985* | (2006.01) | |
| *A61K 31/4155* | (2006.01) | |
| *A61P 3/10* | (2006.01) | |
| *A61K 9/00* | (2006.01) | |

(52) U.S. Cl.
CPC ........ *A61K 31/4985* (2013.01); *A61K 9/0053* (2013.01); *A61K 31/4155* (2013.01); *A61P 3/10* (2018.01)

(58) Field of Classification Search
CPC .............. A61K 31/4985; A61K 9/0053; A61K 31/4155; A61P 3/10
See application file for complete search history.

(56) References Cited

U.S. PATENT DOCUMENTS

| | | | | |
|---|---|---|---|---|
| 7,812,048 B2 * | 10/2010 | Shi | ...... | C07D 233/90 514/400 |
| 11,266,630 B2 * | 8/2022 | Chen | ...... | A61K 31/426 |
| 2019/0328713 A1 | 10/2019 | Chen et al. | | |

FOREIGN PATENT DOCUMENTS

| | | |
|---|---|---|
| CN | 107854435 A | 3/2018 |
| EP | 3804715 A1 | 4/2021 |
| WO | WO 2006/125972 A1 | 11/2006 |
| WO | WO 2013/173417 A2 | 11/2013 |
| WO | WO 2019/228365 A1 | 5/2019 |

OTHER PUBLICATIONS

Scheen, "Pharmacotherapy of 'treatment resistant' type 2 diabetes," *Expert Opinion on Pharmacotherapy*, 18(5):503-515 (2017).
Stone et al., "Quality of Care of People With Type 2 Diabetes in Eight European Countries: Findings from the Guideline Adherence to Enhance Care (GUIDANCE) study," *Diabetes Care*, 36:2628-2638 (2013).
Xu et al., "Safety, tolerability, pharmacokinetics, and pharmacodynamics of novel GK activator HMS5552: Results from a First-In-Human Single Ascending Dose Study," *Drug Design, Development and Therapy*, 10:1619-1626 (2016).
NCT03790839: Drug Interaction Study Between Dorzagliatin and Sitagliptin, version 1, submitted Dec. 28, 2018, downloaded Apr. 14, 2021 from internet: https://www.clinicaltrials.gov/ct2/history/NCT03790839?V_1=View#StudyPageTop.
NCT03790839: Drug Interaction Study Between Dorzagliatin and Sitagliptin, version 2, submitted Sep. 22, 2019, downloaded Apr. 14, 2021 from internet: https://www.clinicaltrials.gov/ct2/history/NCT03790839?V_2=View#StudyPageTop.
Hua Medicine, "Hua Medicine Initiates First Combination Study of Dorzagliatin with a DPP-4 Inhibitor in the United States", Feb. 2, 2019, downloaded Apr. 15, 2021 from internet: https://www.huamedicine.com/En/news-153.

\* cited by examiner

Primary Examiner — Michael Barker
Assistant Examiner — Jed A Kucharczk
(74) Attorney, Agent, or Firm — Jones Day

(57) ABSTRACT

Provided herein is a method of treating, preventing, or ameliorating one or more symptoms of an untreated or treatment-resistant diabetes with a glucokinase activator, optionally in combination with a dipeptidyl peptidase-4 inhibitor.

29 Claims, No Drawings

TREATING UNTREATED OR TREATMENT-RESISTANT DIABETES WITH GLUCOKINASE ACTIVATOR

CROSS-REFERENCE TO RELATED APPLICATIONS

This application claims the benefit of U.S. Provisional Application No. 62/968,441, filed Jan. 31, 2020, the entirety of which is incorporated herein by reference.

FIELD

Provided herein is a method of treating, preventing, or ameliorating one or more symptoms of an untreated or treatment-resistant diabetes with a glucokinase activator, optionally in combination with a dipeptidyl peptidase-4 inhibitor.

BACKGROUND

Diabetes mellitus is a major health issue in the world. Nearly half a billion people are living with diabetes worldwide in 2019. *IDF Diabetes Atlas;* 9th ed.; International Diabetes Federation; 2019. Type 2 diabetes, i.e., non-insulin dependent diabetes mellitus (NIDDM), accounts for more than 90% of diabetes worldwide. Id. Type 2 diabetes is a hyperglycemic, chronic, metabolic dysfunction resulting from an imbalance of blood glucose homeostasis in the human body caused by insulin secretion disorder and insulin resistance. The blood glucose balance of the human body is mainly coordinated by two hormones that control blood glucose, including insulin and glucagon. Glucagon-like peptide-1 (GLP-1) is involved in the regulation of insulin secretion. GLP-1 is also a therapeutic drug for diabetes that plays an important role in the blood glucose balance in human body. Insulin and GLP-1 analogues have become important drugs for the treatment of diabetes.

Glucokinase (GK) plays a central role in stabilizing the blood glucose balance in human body. GK as a glucose sensor in glucose homeostasis, regulates the secretion of glucagon, insulin, and GLP-1 stimulated by glucose. GK is mainly distributed in the liver, where it rapidly converts glucose into hepatic glycogen for storage in response to elevated blood glucose and meanwhile lowers the glucose level in the blood. Defect of glucokinase causes impaired glucose tolerance (IGT) and type 2 diabetes. However, there is currently no glucokinase activator approved for clinical use.

Because of the progressive failure of beta cells, type-2 diabetes is an evolving disease that requires progressive treatment intensification over time in order to control glucose adequately. Scheen, *Expert Opin. Pharmacother.* 2017, 18, 503-515. Treatment resistance is common and a major challenge in managing type-2 diabetes. Id.; Stone et al., *Diabetes Care* 2013, 36, 2628-2638. A large number of type-2 diabetes patients have poor glycemic control despite oral therapy combining metformin, a sulfonylurea, and another glucose-lowering agent. Scheen, *Expert Opin. Pharmacother.* 2017, 18, 503-515. Therefore, there is a clinical need to be met in the field of a diabetes, particularly in treating a treatment-resistant diabetes.

SUMMARY OF THE DISCLOSURE

Provided herein is a method of treating an untreated or treatment-resistant diabetes, comprising administering to a subject in need thereof (i) a therapeutically effective amount of a glucokinase activator and (ii) optionally a therapeutically effective amount of a dipeptidyl peptidase-4 (DPP-4) inhibitor.

Also provided herein is a method of treating an untreated or treatment-resistant diabetes, comprising administering to a subject in need thereof a therapeutically effective amount of a glucokinase activator.

Furthermore, provided herein is a method of treating an untreated or treatment-resistant diabetes, comprising administering to a subject in need thereof (i) a therapeutically effective amount of a glucokinase activator and (ii) a therapeutically effective amount of a dipeptidyl peptidase-4 (DPP-4) inhibitor.

Additionally provided herein is a method of treating an untreated or treatment-resistant diabetes, comprising administering to a subject in need thereof a therapeutically effective amount of a glucokinase activator, wherein the glucokinase activator is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof, or a pharmaceutically acceptable salt, solvate, hydrate, or prodrug thereof.

Provided herein is a method of treating an untreated or treatment-resistant diabetes, comprising administering to a subject in need thereof (i) a therapeutically effective amount of a glucokinase activator and (ii) a therapeutically effective amount of a dipeptidyl peptidase-4 (DPP-4) inhibitor; wherein the glucokinase activator is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof, or a pharmaceutically acceptable salt, solvate, hydrate, or prodrug thereof.

DETAILED DESCRIPTION

To facilitate understanding of the disclosure set forth herein, a number of terms are defined below.

Generally, the nomenclature used herein and the laboratory procedures in organic chemistry, medicinal chemistry, biochemistry, biology, and pharmacology described herein are those well-known and commonly employed in the art. Unless defined otherwise, all technical and scientific terms used herein generally have the same meaning as commonly understood by one of ordinary skill in the art to which this disclosure belongs.

The term "subject" refers to an animal, including, but not limited to, a primate (e.g., human), cow, pig, sheep, goat, horse, dog, cat, rabbit, rat, or mouse. The terms "subject" and "patient" are used interchangeably herein in reference, for example, to a mammalian subject, such as a human subject. In one embodiment, the subject is a human.

The terms "treat," "treating," and "treatment" are meant to include alleviating or abrogating a disorder, disease, or condition, or one or more of the symptoms associated with the disorder, disease, or condition; or alleviating or eradicating the cause(s) of the disorder, disease, or condition itself.

The terms "prevent," "preventing," and "prevention" are meant to include a method of delaying and/or precluding the onset of a disorder, disease, or condition, and/or its attendant symptoms; barring a subject from acquiring a disorder, disease, or condition; or reducing a subject's risk of acquiring a disorder, disease, or condition.

The terms "alleviate" and "alleviating" refer to easing or reducing one or more symptoms (e.g., pain) of a disorder, disease, or condition. The terms can also refer to reducing adverse effects associated with an active ingredient. Sometimes, the beneficial effects that a subject derives from a prophylactic or therapeutic agent do not result in a cure of the disorder, disease, or condition.

The term "therapeutically effective amount" or "effective amount" is meant to include the amount of a compound that, when administered, is sufficient to prevent development of, or alleviate to some extent, one or more of the symptoms of the disorder, disease, or condition being treated. The term "therapeutically effective amount" or "effective amount" also refers to the amount of a compound that is sufficient to elicit a biological or medical response of a biological molecule (e.g., a protein, enzyme, RNA, or DNA), cell, tissue, system, animal, or human, which is being sought by a researcher, veterinarian, medical doctor, or clinician.

The term "pharmaceutically acceptable carrier," "pharmaceutically acceptable excipient," "physiologically acceptable carrier," or "physiologically acceptable excipient" refers to a pharmaceutically acceptable material, composition, or vehicle, such as a liquid or solid filler, diluent, solvent, or encapsulating material. In one embodiment, each component is "pharmaceutically acceptable" in the sense of being compatible with the other ingredients of a pharmaceutical formulation, and suitable for use in contact with the tissue or organ of a subject (e.g., a human or an animal) without excessive toxicity, irritation, allergic response, immunogenicity, or other problems or complications, commensurate with a reasonable benefit/risk ratio. See, e.g., *Remington: The Science and Practice of Pharmacy,* 22nd ed.; Allen Ed.: Philadelphia, P A, 2012; *Handbook of Pharmaceutical Excipients,* 8th ed.; Sheskey et al., Eds.; The Pharmaceutical Press: 2017; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, F L, 2009.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

In certain embodiments, "optically active" and "enantiomerically active" refer to a collection of molecules, which has an enantiomeric excess of no less than about 80%, no less than about 90%, no less than about 91%, no less than about 92%, no less than about 93%, no less than about 94%, no less than about 95%, no less than about 96%, no less than about 97%, no less than about 98%, no less than about 99%, no less than about 99.5%, or no less than about 99.8%. In certain embodiments, an optically active compound comprises about 95% or more of one enantiomer and about 5% or less of the other enantiomer based on the total weight of the enantiomeric mixture in question. In certain embodiments, an optically active compound comprises about 98% or more of one enantiomer and about 2% or less of the other enantiomer based on the total weight of the enantiomeric mixture in question. In certain embodiments, an optically active compound comprises about 99% or more of one enantiomer and about 1% or less of the other enantiomer based on the total weight of the enantiomeric mixture in question.

In describing an optically active compound, the prefixes R and S are used to denote the absolute configuration of the compound about its chiral center(s). The (+) and (−) are used to denote the optical rotation of the compound, that is, the direction in which a plane of polarized light is rotated by the optically active compound. The (−) prefix indicates that the compound is levorotatory, that is, the compound rotates the plane of polarized light to the left or counterclockwise. The (+) prefix indicates that the compound is dextrorotatory, that is, the compound rotates the plane of polarized light to the right or clockwise. However, the sign of optical rotation, (+) and (−), is not related to the absolute configuration of the compound, R and S.

The term "isotopically enriched" refers to a compound that contains an unnatural proportion of an isotope at one or more of the atoms that constitute such a compound. In certain embodiments, an isotopically enriched compound contains unnatural proportions of one or more isotopes, including, but not limited to, hydrogen (H), deuterium ($^{2}$H), tritium ($^{3}$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I) iodine-129 ($^{129}$I), and iodine-131 ($^{131}$I). In certain embodiments, an isotopically enriched compound is in a stable form, that is, non-radioactive. In certain embodiments, an isotopically enriched compound contains unnatural proportions of one or more isotopes, including, but not limited to, hydrogen (H), deuterium ($^{2}$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 ($^{18}$O), fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, an isotopically enriched compound is in an unstable form, that is, radioactive. In certain embodiments, an isotopically enriched compound contains unnatural proportions of one or more isotopes, including, but not limited to, tritium (3H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). It will be understood that, in a compound as provided herein, any hydrogen can be $^{2}$H, as example, or any carbon can be $^{13}$C, as example, or any nitrogen can be $^{15}$N, as example, or any oxygen can be $^{18}$O, as example, where feasible according to the judgment of one of ordinary skill in the art.

The term "isotopic enrichment" refers to the percentage of incorporation of a less prevalent isotope (e.g., D for deuterium or hydrogen-2) of an element at a given position in a molecule in the place of a more prevalent isotope (e.g., $^{1}$H for protium or hydrogen-1) of the element. As used herein, when an atom at a particular position in a molecule is designated as a particular less prevalent isotope, it is understood that the abundance of that isotope at that position is substantially greater than its natural abundance.

The term "isotopic enrichment factor" refers the ratio between the isotopic abundance in an isotopically enriched compound and the natural abundance of a specific isotope.

The term "deuterium enrichment" refers to the percentage of incorporation of deuterium at a given position in a molecule in the place of hydrogen. For example, deuterium enrichment of 1% at a given position means that 1% of molecules in a given sample contain deuterium at the specified position. Because the naturally occurring distribution of deuterium is about 0.0156% on average, deuterium enrichment at any position in a compound synthesized using non-enriched starting materials is about 0.0156% on average. As used herein, when a particular position in an isotopically enriched compound is designated as having deuterium, it is understood that the abundance of deuterium at that position in the compound is substantially greater than its natural abundance (0.0156%).

The terms "substantially pure" and "substantially homogeneous" mean sufficiently homogeneous to appear free of readily detectable impurities as determined by standard analytical methods used by one of ordinary skill in the art, including, but not limited to, thin layer chromatography (TLC), gel electrophoresis, high performance liquid chromatography (HPLC), gas chromatography (GC), nuclear magnetic resonance (NMR), and mass spectrometry (MS); or sufficiently pure such that further purification would not detectably alter the physical, chemical, biological, and/or pharmacological properties, such as enzymatic and biological activities, of the substance. In certain embodiments, "substantially pure" or "substantially homogeneous" refers to a collection of molecules, wherein at least about 95%, at least about 96%, at least about 97%, at least about 98%, at least about 99%, or at least about 99.5% by weight of the molecules are a single compound, including a single enantiomer, a racemic mixture, or a mixture of enantiomers, as determined by standard analytical methods. As used herein, when an atom at a particular position in an isotopically enriched molecule is designated as a particular less prevalent isotope, a molecule that contains other than the designated isotope at the specified position is an impurity with respect to the isotopically enriched compound. Thus, for a deuterated compound that has an atom at a particular position designated as deuterium, a compound that contains a protium at the same position is an impurity.

The term "solvate" refers to a complex or aggregate formed by one or more molecules of a solute, e.g., a compound provided herein, and one or more molecules of a solvent, which are present in stoichiometric or non-stoichiometric amount. Suitable solvents include, but are not limited to, water, methanol, ethanol, n-propanol, isopropanol, and acetic acid. In certain embodiments, the solvent is pharmaceutically acceptable. In one embodiment, the complex or aggregate is in a crystalline form. In another embodiment, the complex or aggregate is in a noncrystalline form. Where the solvent is water, the solvate is a hydrate. Examples of hydrates include, but are not limited to, a hemihydrate, monohydrate, dihydrate, trihydrate, tetrahydrate, and pentahydrate.

The phrase "a tautomer, a mixture of two or more tautomers, or an isotopic variant thereof; or a pharmaceutically acceptable salt, solvate, hydrate, or prodrug thereof" has the same meaning as the phrase "(i) a tautomer, a mixture of two or more tautomers, or an isotopic variant of the compound referenced therein; or (ii) a pharmaceutically acceptable salt, solvate, hydrate, or prodrug of the compound referenced therein, or (iii) a pharmaceutically acceptable salt, solvate, hydrate, or prodrug of a tautomer, a mixture of two or more tautomers, or an isotopic variant of the compound referenced therein."

Methods of Treatment

In one embodiment, provided herein is a method of treating an untreated or treatment-resistant diabetes, comprising administering to a subject in need thereof: (i) a therapeutically effective amount of a glucokinase activator (GKA); and (ii) optionally a therapeutically effective amount of a dipeptidyl peptidase-4 (DPP-4) inhibitor.

In another embodiment, provided herein is a method of treating an untreated or treatment-resistant diabetes, comprising administering to a subject in need thereof a therapeutically effective amount of a GKA.

In yet another embodiment, provided herein is a method of treating an untreated or treatment-resistant diabetes, comprising administering to a subject in need thereof: (i) a therapeutically effective amount of a GKA and (ii) a therapeutically effective amount of a DPP-4 inhibitor.

In one embodiment, the GKA is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof, or a pharmaceutically acceptable salt, solvate, hydrate, or prodrug thereof. This GKA is also known as dorzagliatin having the structure shown below.

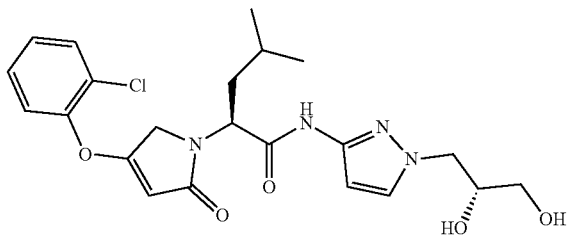 [SMILES: CC(C)C[C@@H](C(=O)Nc1ccn(C[C@@H](O)CO)n1)N1CC(Oc2ccccc2Cl)=CC1=O]

In another embodiment, the GKA is one disclosed in U.S. Pat. No. 7,741,327 B2 or 9,388,168 B2, the disclosure of each of which is incorporated herein by reference in its entirety.

In certain embodiments, the GKA is deuterium-enriched. In certain embodiments, the GKA is carbon-13 enriched. In certain embodiments, the GKA is carbon-14 enriched. In certain embodiments, the GKA contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In certain embodiments, the GKA has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when the GKA at a given position is 100% enriched with the specified isotope. Thus, the maximum isotopic enrichment factor is different for different isotopes. The maximum isotopic enrichment factor is 6,410 for deuterium and 90 for carbon-13.

In certain embodiments, the GKA has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, the GKA has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of the GKA as specified as isotopically enriched has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the GKA as specified as isotopically enriched have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of the GKA is no less than the natural abundance of the isotope specified.

In certain embodiments, at least one of the atoms of the GKA as specified as deuterium-enriched, has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the GKA as specified as deuterium-enriched, have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of the GKA as specified as $^{13}$C-enriched, has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of the GKA as specified as $^{13}$C-enriched, have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, the GKA is isolated or purified. In certain embodiments, the GKA has a purity of at least about 50%, at least about 70%, at least about 80%, at least about 90%, at least about 95%, at least about 98%, at least about 99%, or at least about 99.5% by weight.

The GKA is intended to encompass all possible stereoisomers, unless a particular stereochemistry is specified. Where the GKA contains an alkenyl group, the GKA may exist as one or mixture of geometric cis/trans (or Z/E) isomers. Where structural isomers are interconvertible, the GKA may exist as a single tautomer or a mixture of tautomers. This can take the form of proton tautomerism in the GKA that contains, for example, an imino, keto, or oxime group; or so-called valence tautomerism in the GKA that contain an aromatic moiety. It follows that a single GKA may exhibit more than one type of isomerism.

The GKA can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a GKA in its (R) form is equivalent, for GKAs that undergo epimerization in vivo, to administration of the GSK in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the GKA contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; Wiley-VCH and VHCA, Zurich, 2011.

Suitable acids for use in the preparation of pharmaceutically acceptable salts of the GKA include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of the GKA, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, decanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The GKA may also be provided as a prodrug, which is a functional derivative of the GKA and is readily convertible into the parent GKA in vivo. Prodrugs are often useful because, in some situations, they may be easier to administer than the parent GKA. They may, for instance, be bioavailable by oral administration whereas the parent GKA is not. The prodrug may also have enhanced solubility in pharmaceutical compositions over the parent GKA. A prodrug may be converted into the parent drug by various mechanisms, including enzymatic processes and metabolic hydrolysis.

In certain embodiments, the GKA is formulated as a pharmaceutical composition comprising the GKA and a pharmaceutically acceptable excipient.

The GKA pharmaceutical composition can be formulated in various dosage forms, including, but not limited to, dosage forms for oral, parenteral, and topical administration. The GKA pharmaceutical composition can also be formulated as modified release dosage forms, including delayed-, extended-, prolonged-, sustained-, pulsatile-, controlled-, accelerated-, fast-, targeted-, programmed-release, and gastric retention dosage forms. These dosage forms can be prepared according to conventional methods and techniques known to those skilled in the art. See, e.g., *Remington: The Science and Practice of Pharmacy, supra; Modified-Release Drug Delivery Technology*, 2nd ed.; Rathbone et al., Eds.; Drugs and the Pharmaceutical Sciences 184; CRC Press: Boca Raton, F L, 2008.

In one embodiment, a GKA pharmaceutical composition is formulated in a dosage form for oral administration. In another embodiment, a GKA pharmaceutical composition is formulated in a dosage form for parenteral administration. In yet another embodiment, a GKA pharmaceutical composition is formulated in a dosage form for intravenous administration. In yet another embodiment, a GKA pharmaceutical composition is formulated in a dosage form for intramuscular administration. In yet another embodiment, a GKA pharmaceutical composition is formulated in a dosage form for subcutaneous administration. In still another embodiment, a GKA pharmaceutical composition is formulated in a dosage form for topical administration.

A GKA pharmaceutical composition provided herein can be provided in a unit-dosage form or multiple-dosage form. A unit-dosage form, as used herein, refers to physically discrete a unit suitable for administration to a subject, and packaged individually as is known in the art. Each unit-dose contains a predetermined quantity of an active ingredient(s) (e.g., the GKA described herein) sufficient to produce the desired therapeutic effect, in association with the required pharmaceutical excipient(s). Examples of a unit-dosage form include, but are not limited to, an ampoule, syringe, and individually packaged tablet and capsule. A unit-dosage form may be administered in fractions or multiples thereof. A multiple-dosage form is a plurality of identical unit-dosage forms packaged in a single container to be administered in a segregated unit-dosage form. Examples of a multiple-dosage form include, are not limited to, a vial, bottle of tablets or capsules, or bottle of pints or gallons.

The GKA pharmaceutical composition can be administered at once or multiple times at intervals of time. It is understood that the precise dosage and duration of treatment may vary with the age, weight, and condition of the subject being treated, and may be determined empirically using known testing protocols or by extrapolation from in vivo or in vitro test or diagnostic data. It is further understood that for any particular individual, specific dosage regimens should be adjusted over time according to the subject's need and the professional judgment of the person administering or supervising the administration of the GKA pharmaceutical composition.

In certain embodiments, the GKA pharmaceutical composition contains a GKA described herein (e.g., dorzagliatin) in an amount ranging from about 1 to about 1,000, from about 5 to about 500, from about 10 to about 250, from about 10 to about 150, or from about 20 to about 100 mg per unit (e.g., a tablet). In certain embodiments, the GKA pharmaceutical composition contains a GKA described herein (e.g., dorzagliatin) in an amount ranging from about 1 to about 1,000 mg per unit (e.g., a tablet). In certain embodiments, the GKA pharmaceutical composition contains a GKA described herein (e.g., dorzagliatin) in an amount ranging from about 5 to about 500 mg per unit (e.g., a tablet). In certain embodiments, the GKA pharmaceutical composition contains a GKA described herein (e.g., dorzagliatin) in an amount ranging from about 10 to about 250 mg per unit (e.g., a tablet). In certain embodiments, the GKA pharmaceutical composition contains a GKA described herein (e.g., dorzagliatin) in an amount ranging from about 10 to about 150 mg per unit (e.g., a tablet). In certain embodiments, the GKA pharmaceutical composition contains a GKA described herein (e.g., dorzagliatin) in an amount ranging from about 25 to about 100 mg per unit (e.g., a tablet). In certain embodiments, the GKA pharmaceutical composition contains a GKA described herein (e.g., dorzagliatin) in an amount of about 10, about 20, about 25, about 30, about 40, about 50, about 55, about 60, about 65, about 70, about 75, about 80, about 85, about 90, about 95, about 100, about 110, about 120, about 130, about 140, or about 150 mg per unit (e.g., a tablet). In certain embodiments, the GKA pharmaceutical composition contains a GKA described herein (e.g., dorzagliatin) in an amount of about 25, about 50, about 75, or about 100 mg per unit (e.g., a tablet).

In one embodiment, the GKA pharmaceutical composition (hereinafter, "dorzagliatin formulation") described herein comprises (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof; and a pharmaceutically acceptable excipient.

In another embodiment, the dorzagliatin formulation is one disclosed in U.S. Pat. Appl. Pub. No. 2019/0328713 A1; the disclosure of which is incorporated herein by reference in its entirety.

In certain embodiments, the dorzagliatin formulation is formulated for oral administration. In certain embodiments, the dorzagliatin formulation is formulated as capsule. In certain embodiments, the dorzagliatin formulation is formulated as a tablet. In certain embodiments, the tablet is film-coated.

In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 1 to about 1,000, from about 5 to about 500, from about 10 to about 250, from about 10 to about 150, or from about 20 to about 100 mg per unit (e.g., a tablet). In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 1 to about 1,000 mg per unit (e.g., a tablet). In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 5 to about 500 mg per unit (e.g., a tablet). In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 10 to about 250 mg per unit (e.g., a tablet). In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 10 to about 150 mg per unit (e.g., a tablet). In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount ranging from about 20 to about 100 mg per unit (e.g., a tablet). In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount of about 10, about 25, about 30, about 40, about 50, about 55, about 60, about 65, about 70, about 75, about 80, about 85, about 90, about 95, about 100, about 110, about 120, about 130, about 140, or about 150 mg per unit (e.g., a tablet). In certain embodiments, the dorzagliatin formulation contains (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide in an amount of about 25, about 50, about 75, or about 100 mg per unit (e.g., a tablet).

In certain embodiments, the therapeutically effective amount of the GKA (e.g., dorzagliatin) is ranging from about 0.1 to about 50, from about 0.2 to about 20, from about 0.5 to about 10, or from about 1 to about 5 mg/kg per day. In certain embodiments, the therapeutically effective amount of the GKA (e.g., dorzagliatin) is ranging from about 0.1 to about 50 mg/kg per day. In certain embodiments, the therapeutically effective amount of the GKA (e.g., dorzagliatin) is ranging from about 0.2 to about 20 mg/kg per day. In certain embodiments, the therapeutically effective amount of the GKA (e.g., dorzagliatin) is ranging from about 0.5 to about 10 mg/kg per day. In certain embodiments, the therapeutically effective amount of the GKA (e.g., dorzagliatin) is ranging from about 1 to about 5 mg/kg per day. In certain embodiments, the therapeutically effective amount of the GKA (e.g., dorzagliatin) is about 0.5, about 0.7, about 1, about 1.2, about 1.5, about 1.7, about 2, about 2.2, about 2.5, about 2.7, about 3, about 3.5, about 4, about 4.5, or about 5 mg/kg per day.

In certain embodiments, the therapeutically effective amount of the GKA (e.g., dorzagliatin) is ranging from about 5 to about 1,000, from about 10 to about 500, or from about 20 to about 200 mg per day. In certain embodiments, the therapeutically effective amount of the GKA (e.g., dorzagliatin) is ranging from about 5 to about 1,000 mg per day. In certain embodiments, the therapeutically effective amount of the GKA (e.g., dorzagliatin) is ranging from about 10 to about 500 mg per day. In certain embodiments, the therapeutically effective amount of the GKA (e.g., dorzagliatin) is ranging from about 20 to about 200 mg per day. In certain embodiments, the therapeutically effective amount of the GKA (e.g., dorzagliatin) is about 20, about 40, about 60, about 80, about 100, about 110, about 120, about 130, about 140, about 150, about 160, about 170, about 180, about 190, or about 200 mg per day. In certain embodiments, the therapeutically effective amount of the GKA (e.g., dorzagliatin) is about 25, about 50, or about 75 mg per day.

In certain embodiments, the GKA (e.g., dorzagliatin) is administered once daily (QD), or divided into multiple daily doses such as twice daily (BID), and three times daily (TID). In certain embodiments, the GKA (e.g., dorzagliatin) is administered once daily (QD). In certain embodiments, the GKA (e.g., dorzagliatin) is administered twice daily (BID). In certain embodiments, the GKA (e.g., dorzagliatin) is administered three times daily (TID).

In certain embodiments, the GKA is administered under fasted conditions. In certain embodiments, the GKA is administered without a food. In certain embodiments, the GKA is administered at least about 10, about 20, about 30, about 40, or about 60 min before a meal. In certain embodiments, the GKA is administered at least 1, 2, or 3 hours after a meal.

It will be understood, however, that the specific dose level and frequency of dosage for any particular subject can be varied and will depend upon a variety of factors including the activity of the specific GKA (e.g., e.g., dorzagliatin), the metabolic stability and length of action of the compound, the age, body weight, general health, sex, diet, mode and time of administration, rate of excretion, drug combination, the severity of the particular condition, and the host undergoing therapy.

In one embodiment, the DPP-4 inhibitor is alogliptin, anagliptin, dutogliptin, evogliptin, gemigliptin, gosogliptin, linagliptin, omarigliptin, saxagliptin, sitagliptin, teneligliptin, trelagliptin, or vildagliptin; or a tautomer, a mixture of two or more tautomers, or an isotopic variant thereof; or a pharmaceutically acceptable salt, solvate, hydrate, or prodrug thereof. In another embodiment, the DPP-4 inhibitor is alogliptin, anagliptin, evogliptin, gemigliptin, gosogliptin, linagliptin, omarigliptin, saxagliptin, sitagliptin, teneligliptin, trelagliptin, or vildagliptin; or a tautomer, a mixture of two or more tautomers, or an isotopic variant thereof; or a pharmaceutically acceptable salt, solvate, hydrate, or prodrug thereof. In yet another embodiment, the DPP-4 inhibitor is alogliptin, linagliptin, saxagliptin, or sitagliptin; or a tautomer, a mixture of two or more tautomers, or an isotopic variant thereof; or a pharmaceutically acceptable salt, solvate, hydrate, or prodrug thereof.

In one embodiment, the DPP-4 inhibitor is (R)-2-((6-(3-aminopiperidin-1-yl)-3-methyl-2,4-dioxo-3,4-dihydropyrimidin-1(2H)-yl)methyl)benzonitrile (also known as alogliptin):

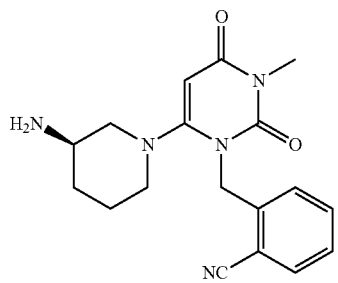 [SMILES: Cn1c(=O)cc(N2CCC[C@@H](N)C2)n(Cc2ccccc2C#N)c1=O]

or a tautomer, a mixture of two or more tautomers, or an isotopic variant thereof; or a pharmaceutically acceptable salt, solvate, hydrate, or prodrug thereof. In certain embodiments, the DPP-4 inhibitor is anagliptin.

In another embodiment, the DPP-4 inhibitor is (S)-N-(2-((2-(2-cyanopyrrolidin-1-yl) -2-oxoethyl)amino)-2-methylpropyl)-2-methylpyrazolo[1,5-a]pyrimidine-6-carboxamide (also known as anaglipitin):

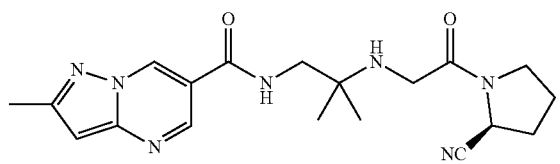 [SMILES: Cc1cc2ncc(C(=O)NCC(C)(C)NCC(=O)N3CCC[C@H]3C#N)cn2n1]

or a tautomer, a mixture of two or more tautomers, or an isotopic variant thereof; or a pharmaceutically acceptable salt, solvate, hydrate, or prodrug thereof. In certain embodiments, the DPP-4 inhibitor is anaglipitin.

In yet another embodiment, the DPP-4 inhibitor is ((2R)-1-(2-(((3R)-pyrrolidin-3-yl)amino)acetyl)pyrrolidin-2-yl)boronic acid (also known as dutogliptin):

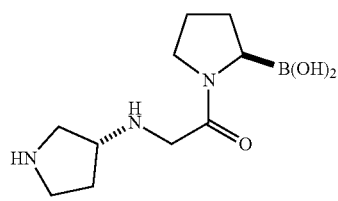

or a tautomer, a mixture of two or more tautomers, or an isotopic variant thereof, or a pharmaceutically acceptable salt, solvate, hydrate, or prodrug thereof. In certain embodiments, the DPP-4 inhibitor is dutogliptin.

In yet another embodiment, the DPP-4 inhibitor is (R)-4-((R)-3-amino-4-(2,4,5-trifluorophenyl)butanoyl)-3-(tert-butoxymethyl)piperazin-2-one (also known as evogliptin):

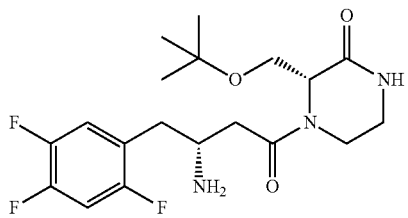 [SMILES: CC(C)(C)OC[C@@H]1C(=O)NCCN1C(=O)C[C@H](N)Cc1cc(F)c(F)cc1F]

or a tautomer, a mixture of two or more tautomers, or an isotopic variant thereof, or a pharmaceutically acceptable salt, solvate, hydrate, or prodrug thereof. In certain embodiments, the DPP-4 inhibitor is evogliptin.

In yet another embodiment, the DPP-4 inhibitor is (S)-1-(2-amino-4-(2,4-bis(trifluoromethyl)-5,8-dihydropyrido[3,4-d]pyrimidin-7(6H)-yl)-4-oxobutyl)-5,5-difluoropiperidin-2-one (also known as gemigliptin):

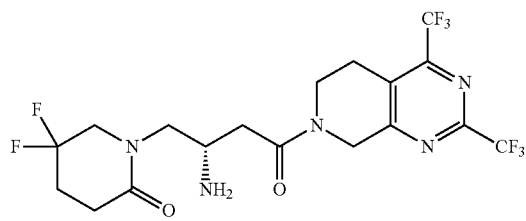 [SMILES: N[C@@H](CC(=O)N1CCc2c(nc(C(F)(F)F)nc2C(F)(F)F)C1)CN1CC(F)(F)CCC1=O]

or a tautomer, a mixture of two or more tautomers, or an isotopic variant thereof, or a pharmaceutically acceptable salt, solvate, hydrate, or prodrug thereof. In certain embodiments, the DPP-4 inhibitor is gemigliptin.

In yet another embodiment, the DPP-4 inhibitor is (3,3-difluoropyrrolidin-1-yl)((2S,4S)-4-(4-(pyrimidin-2-yl)piperazin-1-yl)pyrrolidin-2-yl)methanone (also known as gosogliptin):

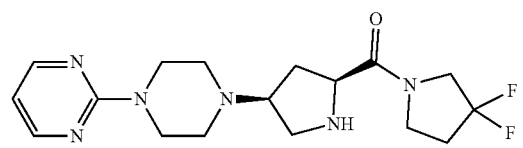 [SMILES: O=C([C@@H]1C[C@H](N2CCN(c3ncccn3)CC2)CN1)N1CCC(F)(F)C1]

or a tautomer, a mixture of two or more tautomers, or an isotopic variant thereof, or a pharmaceutically acceptable salt, solvate, hydrate, or prodrug thereof. In certain embodiments, the DPP-4 inhibitor is gosogliptin.

In yet another embodiment, the DPP-4 inhibitor is (R)-8-(3-aminopiperidin-1-yl)-7-(but-2-yn-1-yl)-3-methyl-1-((4-methylquinazolin-2-yl)methyl)-3,7-dihydro-1H-purine-2,6-dione (also known as linagliptin):

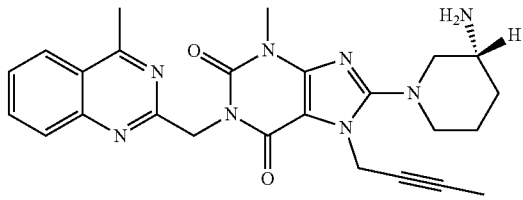 [SMILES: CC#CCn1c(N2CCC[C@@H](N)C2)nc2c1c(=O)n(Cc1nc(C)c3ccccc3n1)c(=O)n2C]

or a tautomer, a mixture of two or more tautomers, or an isotopic variant thereof, or a pharmaceutically acceptable salt, solvate, hydrate, or prodrug thereof. In certain embodiments, the DPP-4 inhibitor is linagliptin.

In yet another embodiment, the DPP-4 inhibitor is (2R,3S,5R)-2-(2,5-difluorophenyl)-5-(2-(methylsulfonyl)-2,6-dihydropyrrolo[3,4-c]pyrazol-5(4H)-yl)tetrahydro-2H-pyran-3-amine (also known as omarigliptin):

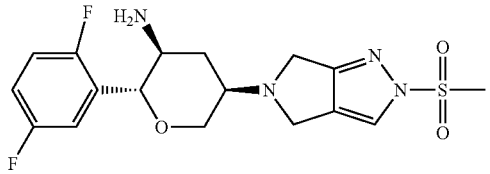 [SMILES: CS(=O)(=O)n1cc2c(n1)CN([C@H]1CO[C@H](c3cc(F)ccc3F)[C@@H](N)C1)C2]

or a tautomer, a mixture of two or more tautomers, or an isotopic variant thereof, or a pharmaceutically acceptable salt, solvate, hydrate, or prodrug thereof. In certain embodiments, the DPP-4 inhibitor is omarigliptin.

In yet another embodiment, the DPP-4 inhibitor is (1S,3S,5S)-2-((S)-2-amino-2-((1r,3R,5R,7S)-3-hydroxyadamantan-1-yl)acetyl)-2-azabicyclo[3.1.0]hexane-3-carbonitrile (also known as saxagliptin):

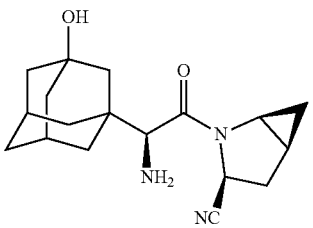 [SMILES: N#C[C@@H]1C[C@@H]2C[C@@H]2N1C(=O)[C@@H](N)C12CC3CC(CC(O)(C3)C1)C2]

or a tautomer, a mixture of two or more tautomers, or an isotopic variant thereof, or a pharmaceutically acceptable salt, solvate, hydrate, or prodrug thereof. In certain embodiments, the DPP-4 inhibitor is saxagliptin.

In yet another embodiment, the DPP-4 inhibitor is (R)-3-amino-1-(3-(trifluoromethyl)-5,6-dihydro-[1,2,4]triazolo[4,3-a]pyrazin-7(8H)-yl)-4-(2,4,5-trifluorophenyl)butan-1-one (also known as sitagliptin):

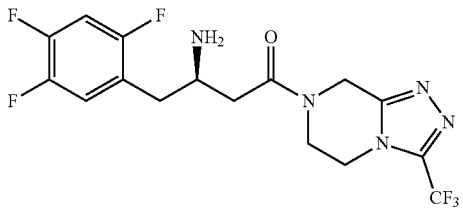 [SMILES: N[C@@H](CC(=O)N1CCn2c(nnc2C(F)(F)F)C1)Cc1cc(F)c(F)cc1F]

or a tautomer, a mixture of two or more tautomers, or an isotopic variant thereof, or a pharmaceutically acceptable salt, solvate, hydrate, or prodrug thereof. In certain embodiments, the DPP-4 inhibitor is sitagliptin.

In yet another embodiment, the DPP-4 inhibitor is ((2S,4S)-4-(4-(3-methyl-1-phenyl-1H-pyrazol-5-yl)piperazin-1-yl)pyrrolidin-2-yl)(thiazolidin-3-yl)methanone (also known as teneligliptin):

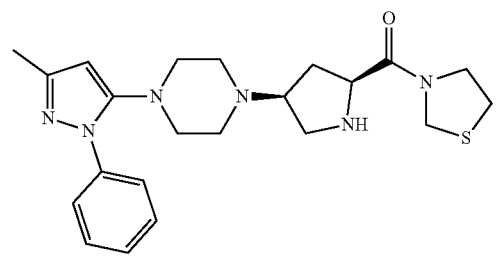 [SMILES: Cc1cc(N2CCN([C@@H]3CN[C@H](C(=O)N4CCSC4)C3)CC2)n(-c2ccccc2)n1]

or a tautomer, a mixture of two or more tautomers, or an isotopic variant thereof, or a pharmaceutically acceptable salt, solvate, hydrate, or prodrug thereof. In certain embodiments, the DPP-4 inhibitor is teneligliptin.

In yet another embodiment, the DPP-4 inhibitor is (R)-2-((6-(3-aminopiperidin-1-yl)-3-methyl-2,4-dioxo-3,4-dihydropyrimidin-1(2H)-yl)methyl)-4-fluorobenzonitrile (also known as trelagliptin):

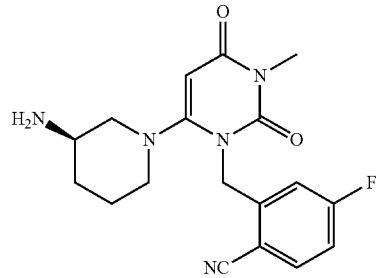 [SMILES: Cn1c(=O)cc(N2CCC[C@@H](N)C2)n(Cc2cc(F)ccc2C#N)c1=O]

or a tautomer, a mixture of two or more tautomers, or an isotopic variant thereof, or a pharmaceutically acceptable salt, solvate, hydrate, or prodrug thereof. In certain embodiments, the DPP-4 inhibitor is trelagliptin.

In still another embodiment, the DPP-4 inhibitor is (S)-1-(((1r,3R,5R,7S)-3-hydroxyadamantan-1-yl)glycyl)pyrrolidine-2-carbonitrilevildagliptin (also known as vildagliptin):

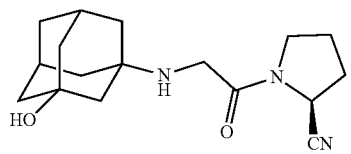 [SMILES: N#C[C@@H]1CCCN1C(=O)CNC12CC3CC(CC(O)(C3)C1)C2]

or a tautomer, a mixture of two or more tautomers, or an isotopic variant thereof, or a pharmaceutically acceptable salt, solvate, hydrate, or prodrug thereof. In certain embodiments, the DPP-4 inhibitor is vildagliptin.

In certain embodiments, the DPP-4 inhibitor is deuterium-enriched. In certain embodiments, the DPP-4 inhibitor is carbon-13 enriched. In certain embodiments, the DPP-4 inhibitor is carbon-14 enriched. In certain embodiments, the DPP-4 inhibitor contains one or more less prevalent isotopes for other elements, including, but not limited to, $^{15}N$ for nitrogen; $^{17}O$ or $^{18}O$ for oxygen, and $^{33}S$, $^{34}S$, or $^{36}S$ for sulfur.

In certain embodiments, the DPP-4 inhibitor has an isotopic enrichment factor of no less than about 5, no less than about 10, no less than about 20, no less than about 30, no less than about 40, no less than about 50, no less than about 60, no less than about 70, no less than about 80, no less than about 90, no less than about 100, no less than about 200, no less than about 500, no less than about 1,000, no less than about 2,000, no less than about 5,000, or no less than about 10,000. In any events, however, an isotopic enrichment factor for a specified isotope is no greater than the maximum isotopic enrichment factor for the specified isotope, which is the isotopic enrichment factor when the DPP-4 inhibitor at a given position is 100% enriched with the specified isotope. Thus, the maximum isotopic enrichment factor is different for different isotopes. The maximum isotopic enrichment factor is 6410 for deuterium and 90 for carbon-13.

In certain embodiments, the DPP-4 inhibitor has a deuterium enrichment factor of no less than about 64 (about 1% deuterium enrichment), no less than about 130 (about 2% deuterium enrichment), no less than about 320 (about 5% deuterium enrichment), no less than about 640 (about 10% deuterium enrichment), no less than about 1,300 (about 20% deuterium enrichment), no less than about 3,200 (about 50% deuterium enrichment), no less than about 4,800 (about 75% deuterium enrichment), no less than about 5,130 (about 80% deuterium enrichment), no less than about 5,450 (about 85% deuterium enrichment), no less than about 5,770 (about 90% deuterium enrichment), no less than about 6,090 (about 95% deuterium enrichment), no less than about 6,220 (about 97% deuterium enrichment), no less than about 6,280 (about 98% deuterium enrichment), no less than about 6,350 (about 99% deuterium enrichment), or no less than about 6,380 (about 99.5% deuterium enrichment). The deuterium enrichment can be determined using conventional analytical methods known to one of ordinary skill in the art, including mass spectrometry and nuclear magnetic resonance spectroscopy.

In certain embodiments, the DPP-4 inhibitor has a carbon-13 enrichment factor of no less than about 1.8 (about 2% carbon-13 enrichment), no less than about 4.5 (about 5% carbon-13 enrichment), no less than about 9 (about 10% carbon-13 enrichment), no less than about 18 (about 20% carbon-13 enrichment), no less than about 45 (about 50% carbon-13 enrichment), no less than about 68 (about 75% carbon-13 enrichment), no less than about 72 (about 80% carbon-13 enrichment), no less than about 77 (about 85% carbon-13 enrichment), no less than about 81 (about 90% carbon-13 enrichment), no less than about 86 (about 95% carbon-13 enrichment), no less than about 87 (about 97% carbon-13 enrichment), no less than about 88 (about 98% carbon-13 enrichment), no less than about 89 (about 99% carbon-13 enrichment), or no less than about 90 (about 99.5% carbon-13 enrichment). The carbon-13 enrichment can be determined using conventional analytical methods known to one of ordinary skill in the art, including mass spectrometry and nuclear magnetic resonance spectroscopy.

In certain embodiments, at least one of the atoms of the DPP-4 inhibitor as specified as isotopically enriched has isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the DPP-4 inhibitor as specified as isotopically enriched have isotopic enrichment of no less than about 1%, no less than about 2%, no less than about 5%, no less than about 10%, no less than about 20%, no less than about 50%, no less than about 70%, no less than about 80%, no less than about 90%, or no less than about 98%. In any events, the isotopic enrichment of the isotopically enriched atom of the DPP-4 inhibitor is no less than the natural abundance of the isotope specified.

In certain embodiments, at least one of the atoms of the DPP-4 inhibitor as specified as deuterium-enriched has deuterium enrichment of no less than about 1%, no less than about 2%, no less than about 5%, no less than about 10%, no less than about 20%, no less than about 50%, no less than about 70%, no less than about 80%, no less than about 90%, or no less than about 98%. In certain embodiments, the atoms of the DPP-4 inhibitor as specified as deuterium-enriched have deuterium enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, at least one of the atoms of the DPP-4 inhibitor as specified as $^{13}$C-enriched has carbon-13 enrichment of no less than about 2%, no less than about 5%, no less than about 10%, no less than about 20%, no less than about 50%, no less than about 70%, no less than about 80%, no less than about 90%, or no less than about 98%. In certain embodiments, the atoms of the DPP-4 inhibitor as specified as $^{13}$C-enriched have carbon-13 enrichment of no less than about 1%, no less than about 2%, no less than about 5%, no less than about 10%, no less than about 20%, no less than about 50%, no less than about 70%, no less than about 80%, no less than about 90%, or no less than about 98%.

In certain embodiments, the DPP-4 inhibitor is isolated or purified. In certain embodiments, the DPP-4 inhibitor has a purity of at least about 50%, at least about 70%, at least about 80%, at least about 90%, at least about 95%, at least about 98%, at least about 99%, or at least about 99.5% by weight.

The DPP-4 inhibitors described herein are intended to encompass all possible stereoisomers, unless a particular stereochemistry is specified. Where the DPP-4 inhibitor contains an alkenyl group, the DPP-4 inhibitor may exist as one or mixture of geometric cis/trans (or Z/E) isomers. Where structural isomers are interconvertible, the DPP-4 inhibitor may exist as a single tautomer or a mixture of tautomers. This can take the form of proton tautomerism in the DPP-4 inhibitor that contains, for example, an imino, keto, or oxime group; or so-called valence tautomerism in the DPP-4 inhibitor that contain an aromatic moiety. It follows that a single DPP-4 inhibitor may exhibit more than one type of isomerism.

The DPP-4 inhibitor can be enantiomerically pure, such as a single enantiomer or a single diastereomer, or be stereoisomeric mixtures, such as a mixture of enantiomers, e.g., a racemic mixture of two enantiomers; or a mixture of two or more diastereomers. As such, one of ordinary skill in the art will recognize that administration of a DPP-4 inhibitor in its (R) form is equivalent, for DPP-4 inhibitors that undergo epimerization in vivo, to administration of the DPP-4 inhibitor in its (S) form. Conventional techniques for the preparation/isolation of individual enantiomers include synthesis from a suitable optically pure precursor, asymmetric synthesis from achiral starting materials, or resolution of an enantiomeric mixture, for example, chiral chromatography, recrystallization, resolution, diastereomeric salt formation, or derivatization into diastereomeric adducts followed by separation.

When the DPP-4 inhibitor contains an acidic or basic moiety, it can also be provided as a pharmaceutically acceptable salt. See, Berge et al., *J. Pharm. Sci.* 1977, 66, 1-19; *Handbook of Pharmaceutical Salts: Properties, Selection, and Use,* 2nd ed.; Stahl and Wermuth Eds.; Wiley-VCH and VHCA, Zurich, 2011.

Suitable acids for use in the preparation of pharmaceutically acceptable salts of the DPP-4 inhibitor include, but are not limited to, acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, boric acid, (+)-camphoric acid, camphorsulfonic acid, (+)-(1S)-camphor-10-sulfonic acid, capric acid, caproic acid, caprylic acid, cinnamic acid, citric acid, cyclamic acid, cyclohexanesulfamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxoglutaric acid, glycolic acid, hippuric acid, hydrobromic acid, hydrochloric acid, hydroiodic acid, (+)-L-lactic acid, (±)-DL-lactic acid, lactobionic acid, lauric acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, perchloric acid, phosphoric acid, L-pyroglutamic acid, saccharic acid, salicylic acid, 4-aminosalicylic acid, sebacic acid, stearic acid, succinic acid, sulfuric acid, tannic acid, (+)-L-tartaric acid, thiocyanic acid, p-toluenesulfonic acid, undecylenic acid, and valeric acid.

Suitable bases for use in the preparation of pharmaceutically acceptable salts of the DPP-4 inhibitor, including, but not limited to, inorganic bases, such as magnesium hydroxide, calcium hydroxide, potassium hydroxide, zinc hydroxide, or sodium hydroxide; and organic bases, such as primary, secondary, tertiary, and quaternary, aliphatic and aromatic amines, including L-arginine, benethamine, benzathine, choline, decanol, diethanolamine, diethylamine, dimethylamine, dipropylamine, diisopropylamine, 2-(diethylamino)-ethanol, ethanolamine, ethylamine, ethylenediamine, isopropylamine, N-methyl-glucamine, hydrabamine, 1H-imidazole, L-lysine, morpholine, 4-(2-hydroxyethyl)-morpholine, methylamine, piperidine, piperazine, propylamine, pyrrolidine, 1-(2-hydroxyethyl)-pyrrolidine, pyridine, quinuclidine, quinoline, isoquinoline, triethanolamine, trimethylamine, triethylamine, N-methyl-D-glucamine, 2-amino-2-(hydroxymethyl)-1,3-propanediol, and tromethamine.

The DPP-4 inhibitor may also be provided as a prodrug, which is a functional derivative of a DPP-4 inhibitor, for example, (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, and is readily convertible into the parent DPP-4 inhibitor in vivo. Prodrugs are often useful because, in some situations, they may be easier to administer than the parent DPP-4 inhibitor. They may, for instance, be bioavailable by oral administration whereas the parent DPP-4 inhibitor is not. The prodrug may also have enhanced solubility in pharmaceutical compositions over the parent DPP-4 inhibitor. A prodrug may be converted into the parent drug by various mechanisms, including enzymatic processes and metabolic hydrolysis.

In certain embodiments, alogliptin or a pharmaceutically acceptable salt is formulated as described in the package insert for NESINA®. In certain embodiments, anagliptin or a pharmaceutically acceptable salt is formulated as described in the package insert for SUINY®. In certain embodiments, evogliptin or a pharmaceutically acceptable salt is formulated as described in the package insert for SUGANON®. In certain embodiments, gemigliptin or a pharmaceutically acceptable salt is formulated as described in the package insert for ZEMIGLO®. In certain embodiments, gosogliptin or a pharmaceutically acceptable salt is formulated as described in the package insert for SATRX®. In certain embodiments, linagliptin or a pharmaceutically acceptable salt is formulated as described in the package insert for TRADJENTA®. In certain embodiments, omarigliptin or a pharmaceutically acceptable salt is formulated as described in the package insert for MARIZEV®. In certain embodiments, saxagliptin or a pharmaceutically acceptable salt is formulated as described in the package insert for ONGLYZA®. In certain embodiments, sitagliptin or a pharmaceutically acceptable salt is formulated as described in the package insert for JANUVIA®. In certain embodiments, vildagliptin or a pharmaceutically acceptable salt is formulated as described in the package insert for GALVUS®. In certain embodiments, teneligliptin or a pharmaceutically acceptable salt is formulated as described in the package insert for TENELIA®. In certain embodiments, trelagliptin or a pharmaceutically acceptable salt is formulated as described in the package insert for ZAFATEK®.

In certain embodiments, the therapeutically effective amount of the DPP-4 inhibitor (e.g., sitagliptin) is ranging from about 1 to about 1,000, from about 10 to about 500, from about 20 to about 250, or from about 50 to about 200 mg per day. In certain embodiments, the therapeutically effective amount of the DPP-4 inhibitor (e.g., sitagliptin) is ranging from about 1 to about 1,000 mg per day. In certain embodiments, the therapeutically effective amount of the DPP-4 inhibitor (e.g., sitagliptin) is ranging from about 10 to about 500 mg per day. In certain embodiments, the therapeutically effective amount of the DPP-4 inhibitor (e.g., sitagliptin) is ranging from about 20 to about 250 mg per day. In certain embodiments, the therapeutically effective amount of the DPP-4 inhibitor (e.g., sitagliptin) is ranging from about 50 to about 200 mg per day. In certain embodiments, the therapeutically effective amount of the DPP-4 inhibitor (e.g., sitagliptin) is about 50, about 60, about 70, about 80, about 90, about 100, about 110, about 120, about 130, about 140, or about 150 mg per day.

In certain embodiments, the DPP-4 inhibitor (e.g., sitagliptin) is administered under fasted conditions. In certain embodiments, the DPP-4 inhibitor (e.g., sitagliptin) is administered without a food. In certain embodiments, the DPP-4 inhibitor (e.g., sitagliptin) is administered at least about 10, about 20, about 30, about 40, or about 60 min before a meal. In certain embodiments, the DPP-4 inhibitor (e.g., sitagliptin) is administered at least 1, 2, or 3 hours after a meal.

In one embodiment, the diabetes is an untreated or treatment-resistant type 1 diabetes. In another embodiment, the diabetes is an untreated or treatment-resistant type 2 diabetes.

In certain embodiments, the diabetes is a diabetes with persistent hyperglycemia. In certain embodiments, the diabetes is a diabetes with a glycated hemoglobin level (HbA1c) of no less than about 7%. In certain embodiments, the diabetes is a diabetes with an HbA1c of no less than about 8%. In certain embodiments, the diabetes is a diabetes with an HbA1c of no less than about 9%. In certain embodiments, the is a diabetes with an HbA1c of no less than about 10%.

In certain embodiments, the diabetes is a diabetes with an HbA1c of no less than about 64 mmol/mol. In certain embodiments, the diabetes is a diabetes with an HbA1c of no less than about 75 mmol/mol. In certain embodiments, the diabetes is a diabetes with an HbA1c of no less than about 86 mmol/mol.

In certain embodiments, the treatment-resistant diabetes is a diabetes with persistent hyperglycemia despite pharmacological treatment with at least three oral glucose-lowering medications. In certain embodiments, the treatment-resistant diabetes is a diabetes with an HbA1c of no less than about 7% despite pharmacological treatment with at least three oral glucose-lowering medications. In certain embodiments, the treatment-resistant diabetes is a diabetes with an HbA1c of no less than about 8% despite pharmacological treatment with at least three oral glucose-lowering medications. In certain embodiments, the treatment-resistant diabetes is a diabetes with an HbA1c of no less than about 9% despite pharmacological treatment with at least three oral glucose-lowering medications. In certain embodiments, the treatment-resistant diabetes is a diabetes with an HbA1c of no less than about 10% despite pharmacological treatment with at least three oral glucose-lowering medications.

In certain embodiments, the treatment-resistant diabetes is a diabetes with an HbA1c of no less than about 64 mmol/mol despite pharmacological treatment with at least three oral glucose-lowering medications. In certain embodiments, the treatment-resistant diabetes is a diabetes with an HbA1c of no less than about 75 mmol/mol despite pharmacological treatment with at least three oral glucose-lowering medications. In certain embodiments, the treatment-resistant diabetes is a diabetes with an HbA1c of no less than about 86 mmol/mol despite pharmacological treatment with at least three oral glucose-lowering medications.

In certain embodiments, the treatment-resistant diabetes is a diabetes with persistent poorly-controlled diabetes despite standard care with three oral glucose-lowering medications.

In one embodiment, the treatment-resistant diabetes is resistant to a DPP-4 inhibitor, a GLP-1 receptor agonist, an insulin, a meglitinide, metformin, a sodium-glucose cotransporter-2 (SGLT-2) inhibitor, a sulfonylurea, a thiazolidinedione, or a combination thereof.

In one embodiment, the treatment-resistant diabetes is resistant to a DPP-4 inhibitor. In another embodiment, the treatment-resistant diabetes is resistant to an SGLT-2 inhibitor. In yet another embodiment, the treatment-resistant diabetes is resistant to metformin. In yet another embodiment, the treatment-resistant diabetes is resistant to a DPP-4 inhibitor and an SGLT-2 inhibitor. In yet another embodiment, the treatment-resistant diabetes is resistant to a DPP-4 inhibitor and metformin. In yet another embodiment, the treatment-resistant diabetes is resistant to an SGLT-2 inhibitor and metformin. In still another embodiment, the treatment-resistant diabetes is resistant to a DPP-4 inhibitor, an SGLT-2 inhibitor, and metformin.

In certain embodiments, the treatment-resistant diabetes is resistant to a DPP-4 inhibitor. In certain embodiments, the treatment-resistant diabetes is resistant to alogliptin, anagliptin, dutogliptin, evogliptin, gemigliptin, gosogliptin, linagliptin, omarigliptin, saxagliptin, sitagliptin, teneligliptin, trelaglitin, or vildagliptin. In certain embodiments, the treatment-resistant diabetes is resistant to alogliptin, anagliptin, evogliptin, gemigliptin, gosogliptin, linagliptin, omarigliptin, saxagliptin, sitagliptin, teneligliptin, trelaglitin, or vildagliptin. In certain embodiments, the treatment-resistant diabetes is resistant to alogliptin, linagliptin, saxagliptin, or sitagliptin.

In certain embodiments, the treatment-resistant diabetes is resistant to a GLP-1 receptor agonist. In certain embodiments, the treatment-resistant diabetes is resistant to albiglutide, dulaglutide, exenatide, liraglutide, lixisenatide, or semaglutide.

In certain embodiments, the treatment-resistant diabetes is resistant to an insulin. In certain embodiments, the treatment-resistant diabetes is resistant to a fast-acting insulin, a short-acting insulin, an intermediate-acting insulin, a long-acting insulin, or an ultra-long acting insulin.

In certain embodiments, the treatment-resistant diabetes is resistant to a meglitinide. In certain embodiments, the treatment-resistant diabetes is resistant to nateglinide or repaglinide.

In certain embodiments, the treatment-resistant diabetes is resistant to an SGLT-2 inhibitor. In certain embodiments, the treatment-resistant diabetes is resistant to canagliflozin, dapagliflozin, empagliflozin, ertugliflozin, ipragliflozin, luseogliflozin, remogliflozin, sergliflozin, or tofogliflozin. In certain embodiments, the treatment-resistant diabetes is resistant to canagliflozin, dapagliflozin, empagliflozin, or ertugliflozin.

In certain embodiments, the treatment-resistant diabetes is resistant to a sulfonylurea. In certain embodiments, the treatment-resistant diabetes is resistant to chlorpropamide, gliclazide, glimepiride, or tolazamide.

In certain embodiments, the treatment-resistant diabetes is resistant to a thiazolidinedione. In certain embodiments, the treatment-resistant diabetes is resistant to balaglitazone, ciglitazone, darglitazone, englitazone, lobeglitazone, netoglitazone, pioglitazone, rivoglitazone, rosiglitazone, or troglitazone. In certain embodiments, the treatment-resistant diabetes is resistant to lobeglitazone, rosiglitazone, or pioglitazone.

In certain embodiments, the subject with a treatment-resistant diabetes fails a monotherapy. In certain embodiments, the subject with a treatment-resistant diabetes fails a dual-agent therapy.

In certain embodiments, the subject is a mammal. In certain embodiments, the subject is a human.

A method provided herein encompasses treating a subject regardless of subject's age, although some diseases are more common in certain age groups.

In one embodiment, provided herein is a method of treating a treatment-resistant diabetes, comprising administering to a subject in need thereof a therapeutically effective amount of dorzagliatin. In certain embodiments, the therapeutically effective amount of dorzagliatin is about 150 mg per day. In certain embodiments, dorzagliatin is administered in an amount of about 75 mg twice daily.

In another embodiment, provided herein is a method of treating a treatment-resistant diabetes, comprising administering to a subject in need thereof a therapeutically effective amount of dorzagliatin and a therapeutically effective amount of sitagliptin. In certain embodiments, the therapeutically effective amount of dorzagliatin is about 150 mg per day and the therapeutically effective amount of sitagliptin is about 100 mg per day. In certain embodiments, dorzagliatin is administered in an amount of 75 mg twice daily and sitagliptin is administered in an amount of about 100 mg daily. In certain embodiments, the therapeutically effective amount of dorzagliatin is about 25, about 50, or about 75 mg per day and the therapeutically effective amount of sitagliptin is about 100 mg per day.

The disclosure will be further understood by the following non-limiting examples.

EXAMPLES

As used herein, the symbols and conventions used in these processes, schemes and examples, regardless of whether a particular abbreviation is specifically defined, are consistent with those used in the contemporary scientific literature, for example, the Journal of the American Chemical Society, the Journal of Medicinal Chemistry, or the Journal of Biological Chemistry. Specifically, but without limitation, the following abbreviations may be used in the examples and throughout the specification: g (grams); mg (milligrams); dL (deciliters); mL (microliters); mM (millimolar); mol (moles); mmol (millimoles); h (hour or hours); and min (minutes).

Example 1

Phase 1, Open-Label, Sequential, Multiple-Dose, Drug-Drug Interaction (DDI) Study of Dorzagliatin and Sitagliptin in Subjects with Type-2 Diabetes Mellitus (T2DM)

This phase I study accessed the pharmacokinetic interaction between dorzagliatin and sitagliptin in T2DM subjects. This study also evaluated the safety and tolerability of dorzagliatin with simultaneous administration of sitagliptin in T2DM subjects. Moreover, this study accessed the pharmacodynamic responses of glucose, GLP-1, glucagon, insulin, and C-peptide following dorzagliatin, sitagliptin, or simultaneous administration of dorzagliatin and sitagliptin in T2DM subjects.

Study drugs were administered according to the dosing scheme summarized in Table 1. Study drugs are each taken 60 (±5) min prior to meals.

TABLE 1

Treatment Scheme

| Day | Sitagliptin | Dorzagliatin | PK Sample Collection |
|---|---|---|---|
| 1-5 | 100 mg (QD) for 5 days | — | Day 5: Sitagliptin alone |
| 6-10 | 100 mg (QD) for 5 days | 75 mg (BID) for 4 days Morning dose only on Day 10 | Day 10: Sitagliptin + Dorzagliatin |
| 11-15 | — | 75 mg (BID) for 4 days Morning dose only on Day 10 | Day 15: Dorzagliatin alone |

Eligible subjects had a minimum 12-day run-in period prior to admission to a clinical research center (CRC), during which time they self-administered sitagliptin (100 mg QD) each morning up until and including Day −2. Subjects completed a diary to record sitagliptin doses taken each day and were advised to monitor their blood glucose levels and report changes in health status to the CRC. A telephone call was placed to all subjects at approximately Day 6 (±2 day) of the run-in period to assess general health and collect adverse event (AE) information.

Following completion of the run-in period, eligible subjects were admitted to the CRC on Day −2, had a total of 18 overnight stays, and were discharged after end-of-study procedures were completed on Day 17 or at early termination. Blood samples for the determination of dorzagliatin and sitagliptin concentrations and corresponding pharmacokinetic (PK) analysis were collected on Days 5, 10 and 15: pre-dose (within 30 min prior to dosing), and 0.25, 0.5, 1, 1.5, 2, 3, 4, 6, 8, 10, 12, 18, and 24 h post dose.

Subjects consumed a 75-gram glucose solution 30 min following study dose administration on Days 5, 10 and 15 in lieu of breakfast. Pharmacodynamic (PD) responses were evaluated by measuring GLP-1 and glucagon levels in plasma, and glucose, insulin, and C-peptide in serum within 60 min prior to oral glucose intake and 0.5, 1, 1.5, 2, 2.5, 3 and 4 h after oral glucose intake.

Safety assessments included monitoring of AEs, blood glucose via glucometer readings, vital signs (blood pressure, pulse rate, respiratory rate, and oral temperature), clinical laboratory findings, resting 12-lead electrocardiograms (ECGs), and physical examination (PE) findings. Vital signs were assessed at screening, on Days −1-15 within 60 min prior to each morning and evening dose, and on Day 17. Blood glucose was measured using a glucometer three times each day on Days −2 (prior to first meal after admission) through 16, within 60 min before each meal and after study drug dosing when applicable. Clinical laboratory evaluations (chemistry, hematology, and urinalysis) were performed at screening, and on Days −1, 5, 10, 15, and 17. A resting 12-lead ECG was completed at screening, on Day −1, and 2 h post-dose on Days 5, 10, 15, and 17. Physical examinations were conducted at screening and on Days −1 and 17.

Subjects who terminated study participation early had Day 17 assessments performed, if possible, prior to discharge from the CRC.

Eligible subjects for the study were subjects diagnosed with T2DM at least 3 months prior to screening and were taking at the time a stable dose of either of the following therapy with no change in the dose for at least 4 weeks prior to screening: (i) ≥1000 mg per day of metformin; (ii) a DPP-4 inhibitor; (iii) an SGLT-2 inhibitor; (iv) metformin plus a DPP-4 inhibitor; (v) metformin plus an SGLT-2 inhibitor. Subjects must agree to change their therapy to 100 mg sitagliptin QD for at least 14 days prior to dosing on Day 1. Additional inclusion criteria for the eligible subjects included (i) in stable general health as determined by an investigator at screening evaluation performed no more than 42 days prior to dosing on Day 1; (ii) male and/or female subjects between the ages of 30 and 65 years; (iii) body mass index (BMI) of 19 to 38 kg/m$^2$, inclusive, at screening; (iv) fasting C-peptide test result >0.3 nmol/L (>0.90 ng/mL); (v) HbA1c≥7% and ≤10.5%; and (vi) nonsmoker, defined as not having smoked or used any form of tobacco for more than 6 months prior to screening.

The study excluded those with (i) fasting blood glucose at screening or Day −1≤110 or ≥270 mg/dL (one repeat screening fasting blood glucose allowed); (ii) type-1 diabetes mellitus, or latent autoimmune diabetes in adults; diabetic neuropathy, retinopathy or nephropathy; (iii) reported incidence of severe hypoglycemia, defined by denoting severe cognitive impairment requiring external assistance for recovery, within 3 months prior to screening and/or within 3 months prior to dosing on Day 1; (iv) known contraindications to sitagliptin; (v) estimated glomerular filtration rate (eGFR)≤60 mL/min/1.73 m$^2$; (vi) acute or chronic metabolic acidosis, including diabetic ketoacidosis; (vii) any reported hypersensitivity (anaphylaxis and angioedema) or intolerance to sitagliptin; (viii) antidiabetic treatment with insulin, sulfonylureas, thiazolidinediones or GLP-1 agonist within 3 months prior to screening; (ix) systolic blood pressure <90 or >160 mmHg or diastolic blood pressure <60 or >100 mmHg at screening (may be repeated once); (x) uncontrolled hypertriglyceridemia >500 mg/dL; and (xi) use of herbal (including St John's Wort, herbal teas, garlic extracts) within 14 d prior to dosing. No drugs known to be CYP3A4 inhibitors or inducers are allowed.

Fifteen eligible subjects were enrolled singly or in groups and fourteen of them completed the study.

Dorzagliatin was provided as a film-coated tablets in 75 mg strength for oral administration 60 min prior to a meal.

Sitagliptin was provided as JANUVIA® 100 mg tablets for oral administration 60 min prior to a meal. The total duration of participation in the study for each subject was about 59 days (up to 28-day screening period, 12-day run-in period, and 19-day in-clinic period).

Safety assessments included monitoring of AEs, blood glucose via glucometer readings, vital signs (blood pressure, pulse rate, respiratory rate and oral temperature), clinical laboratory findings, 12-lead ECGs, and PE findings.

The plasma concentration-time data for dorzagliatin and sitagliptin were analyzed using noncompartmental methods to calculate pharmacokinetic parameters.

Sitagliptin did not have a significant effect on dorzagliatin PK parameters based on the analysis of plasma dorzagliatin $C_{max}$ and $AUC_{0-24h}$. Least squares geometric means for $C_{max}$ were 833 and 814 for dorzagliatin in combination with sitagliptin and dorzagliatin alone, respectively, with a percent ratio of geometric means (GMR) of 102% (90% CI: 87, 120). Least squares geometric means for $AUC_{0-24h}$ were 6,593 and 6,571 for dorzagliatin in combination with sitagliptin and dorzagliatin alone, respectively, with a percent GMR of 100% (90% CI: 96, 105). A lack of a significant drug-drug interaction for the effect of sitagliptin on dorzagliatin PK parameters was supported by the percent GMR 90% CI for dorzagliatin $C_{max}$ and $AUC_{0-24h}$ being fully contained within the 80.00 to 125.00% boundaries.

Dorzagliatin did not have a significant effect on sitagliptin PK parameters based on the analysis of plasma sitagliptin $C_{max}$ and $AUC_{0-24h}$. Least squares geometric means for $C_{max}$ were 403 and 410 for sitagliptin in combination with dorzagliatin and sitagliptin alone, respectively, with a percent GMR of 98% (90% CI: 84, 115). Least squares geometric means for $AUC_{0-24h}$ were 2,722 and 2,938 for sitagliptin in combination with dorzagliatin and sitagliptin alone, respectively, with a percent GMR of 93% (90% CI: 86, 100). A lack of a significant drug-drug interaction for the effect of dorzagliatin on sitagliptin PK parameters is supported by the percent GMR 90% CI for sitagliptin $C_{max}$ and $AUC_{0-24h}$ being fully contained within the 80.00 to 125.00% boundaries.

Following the oral glucose tolerance test (OGTT), combination administration of sitagliptin and dorzagliatin achieved a larger glucose reduction effect than administration of either sitagliptin or dorzagliatin treatment alone based on the analysis of glucose PD parameters (baseline corrected $AUEC_{0-4h}$, $CE_{max}$, and $CE_{av}$) as summarized in Table 2.

TABLE 2

Glucose Response

| Parameter | Statistic | Sitagliptin | Sitagliptin + Dorzagliatin | Dorzagliatin |
|---|---|---|---|---|
| $CE_{max}$ (mg/dL) | n | 9 | 15 | 14 |
| | Mean (SD) | 165 (35) | 142 (45) | 163 (39) |
| | GMR (%) | 87 | | 83 |
| | P-value | 0.056 | | 0.054 |
| $AUEC_{0-4h}$ (h · mg/dL] | n | 9 | 15 | 14 |
| | Mean (SD) | 378 (88) | 253 (116) | 339 (124) |
| | GMR (%) | 65 | | 69 |
| | P-value | 0.0077 | | 0.0092 |
| $CE_{av}$ (mg/dL) | n | 9 | 15 | 14 |
| | Mean (SD) | 94.5 (22) | 63 (29) | 84.8 (31) |
| | GMR (%) | 65 | | 69 |
| | P-value | 0.0076 | | 0.0092 |

As summarized in Table 3, baseline corrected $AUEC_{0-4h}$, $CE_{max}$, and $CE_{av}$ of insulin trended to be higher after combination administration of sitagliptin and dorzagliatin than after sitagliptin and dorzagliatin monotherapy.

TABLE 3

Insulin Response

| Parameter | Statistic | Sitagliptin | Sitagliptin + Dorzagliatin | Dorzagliatin |
|---|---|---|---|---|
| $CE_{max}$ (mg/dL) | n | 14 | 14 | 14 |
| | Mean (SD) | 62 (40) | 71 (58) | 49 (30) |
| | GMR (%) | 125 | | 146 |
| | P-value | 0.075 | | 0.011 |
| $AUEC_{0-4h}$ (h · mg/dL] | n | 14 | 14 | 14 |
| | Mean (SD) | 128 (70) | 136 (103) | 91 (53) |
| | GMR (%) | 110 | | 159 |
| | P-value | 0.42 | | 0.0032 |
| $CE_{av}$ (mg/dL) | n | 14 | 14 | 14 |
| | Mean (SD) | 32 (17) | 34 (26) | 23 (13) |
| | GMR (%) | 110 | | 159 |
| | P-value | 0.42 | | 0.0033 |

As summarized in Table 4, baseline corrected $AUEC_{0-4h}$, $CE_{max}$, and $CE_{av}$ of C-peptide following combination administration of sitagliptin and dorzagliatin were numerically higher than those for administration of either sitagliptin or dorzagliatin alone.

TABLE 4

C-peptide Response

| Parameter | Statistic | Sitagliptin | Sitagliptin + Dorzagliatin | Dorzagliatin |
|---|---|---|---|---|
| $CE_{max}$ (mg/dL) | n | 13 | 15 | 14 |
| | Mean (SD) | 5.1 (2.4) | 6.3 (3.8) | 4.2 (1.9) |
| | GMR (%) | 125 | | 145 |
| | P-value | 0.021 | | 0.0016 |
| $AUEC_{0-4h}$ (h · mg/dL] | n | 13 | 15 | 14 |
| | Mean (SD) | 12 (5.4) | 14 (7.2) | 9.8 (3.9) |
| | GMR (%) | 119 | | 143 |
| | P-value | 0.058 | | 0.0006 |
| $CE_{av}$ (mg/dL) | n | 13 | 15 | 14 |
| | Mean (SD) | 3.0 (1.3) | 3.6 (1.8) | 2.5 (0.97) |
| | GMR (%) | 119 | | 143 |
| | P-value | 0.059 | | 0.0006 |

The examples set forth above are provided to give those of ordinary skill in the art with a complete disclosure and description of how to make and use the claimed embodiments, and are not intended to limit the scope of what is disclosed herein. Modifications that are obvious to persons of skill in the art are intended to be within the scope of the following claims. All publications, patents, and patent applications cited in this specification are incorporated herein by reference as if each such publication, patent or patent application were specifically and individually indicated to be incorporated herein by reference.

What is claimed is:

1. A method of treating a treatment-resistant diabetes, comprising administering to a subject in need thereof a therapeutically effective amount of a glucokinase activator, wherein the glucokinase activator is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide, or a tautomer, a mixture of two or more tautomers, or an isotopic variant thereof; or a pharmaceutically acceptable salt, solvate, hydrate, or prodrug thereof.

2. The method of claim 1, further comprising administering to the subject a therapeutically effective amount of a dipeptidyl peptidase-4 inhibitor.

3. The method of claim 1, wherein the glucokinase activator is (S)-2-(4-(2-chlorophenoxy)-2-oxo-2,5-dihydro-1H-pyrrol-1-yl)-N-(1-((R)-2,3-dihydroxypropyl)-1H-pyrazol-3-yl)-4-methylpentanamide.

4. The method of claim 1, wherein the therapeutically effective amount of the glucokinase activator is ranging from 0.1 to 50 mg/kg per day.

5. The method of claim 1, wherein the therapeutically effective amount of the glucokinase activator is ranging from 5 to 1,000 mg per day.

6. The method of claim 1, wherein the therapeutically effective amount of the glucokinase activator is 150 mg per day.

7. The method of claim 1, wherein the glucokinase activator is administered orally.

8. The method of claim 1, wherein the glucokinase activator is administered orally as a tablet.

9. The method of claim 1, wherein the glucokinase activator is administered twice a day.

10. The method of claim 2, wherein the dipeptidyl peptidase-4 inhibitor is alogliptin, anagliptin, dutogliptin, evogliptin, gemigliptin, gosogliptin, linagliptin, omarigliptin, saxagliptin, sitagliptin, teneligliptin, trelagliptin, or vildagliptin; or a tautomer, a mixture of two or more tautomers, or an isotopic variant thereof; or a pharmaceutically acceptable salt, solvate, hydrate, or prodrug thereof.

11. The method of claim 2, wherein the dipeptidyl peptidase-4 inhibitor is alogliptin, linagliptin, saxagliptin, or sitagliptin; or a tautomer, a mixture of two or more tautomers, or an isotopic variant thereof; or a pharmaceutically acceptable salt, solvate, hydrate, or prodrug thereof.

12. The method of claim 2, wherein the dipeptidyl peptidase-4 inhibitor is sitagliptin.

13. The method of claim 2, wherein the therapeutically effective amount of the dipeptidyl peptidase-4 inhibitor is ranging from 1 to 1,000 mg per day.

14. The method of claim 2, wherein the therapeutically effective amount of the dipeptidyl peptidase-4 inhibitor is 100 mg per day.

15. The method of claim 2, wherein the dipeptidyl peptidase-4 inhibitor is administered orally.

16. The method of claim 2, wherein the dipeptidyl peptidase-4 inhibitor is administered once a day.

17. The method of claim 1, wherein the treatment-resistant diabetes is a treatment-resistant type-2 diabetes.

18. The method of claim 1, wherein the treatment-resistant diabetes is a diabetes with persistent hyperglycemia.

19. The method of claim 1, wherein the treatment-resistant diabetes is a diabetes with persistent hyperglycemia despite pharmacological treatment with at least three oral glucose-lowering medications.

20. The method of claim 1, wherein the treatment-resistant diabetes is a diabetes with persistent poorly-controlled diabetes despite standard care with three oral glucose-lowering medications.

21. The method of claim 1, wherein the treatment-resistant diabetes is a diabetes with a glycated hemoglobin level (HbA1c) of no less than about 7%.

22. The method of claim 1, wherein the treatment-resistant diabetes is a diabetes with an HbA1c of no less than about 64 mmol/mol.

23. The method of claim 1, wherein the treatment-resistant diabetes is resistant to a dipeptidyl peptidase-4 inhibitor, a GLP-1 receptor agonist, an insulin, a meglitinide, metformin, a sodium-glucose cotransporter-2 inhibitor, a sulfonylurea, a thiazolidinedione, or a combination thereof.

24. The method of claim 1, wherein the treatment-resistant diabetes is resistant to a dipeptidyl peptidase-4 inhibitor, metformin, a sodium-glucose cotransporter-2 inhibitor, or a combination thereof.

25. The method of claim 1, wherein the treatment-resistant diabetes is resistant to metformin.

26. The method of claim 1, wherein the treatment-resistant diabetes is resistant to a sodium-glucose cotransporter-2 inhibitor.

27. The method of claim 1, wherein the treatment-resistant diabetes is resistant to a dipeptidyl peptidase-4 inhibitor.

28. The method of claim 1, wherein the treatment-resistant diabetes is resistant to a sulfonylurea.

29. The method of claim 1, wherein the subject is a human.

* * * * *